United States Patent

Borzatta et al.

[11] Patent Number: 5,187,275
[45] Date of Patent: Feb. 16, 1993

[54] PIPERIDINE-TRIAZINE COMPOUNDS

[75] Inventors: Valerio Borzatta; Roberto Scrima; Graziano Vignali, all of Bologna, Italy

[73] Assignee: Ciba-Geigy Corporation, Ardsley, N.Y.

[21] Appl. No.: 769,982

[22] Filed: Sep. 30, 1991

[30] Foreign Application Priority Data

Oct. 3, 1990 [IT] Italy ............... 21632 A/90

[51] Int. Cl.$^5$ .................. C07D 401/12; C07D 401/14
[52] U.S. Cl. .................... 544/207; 544/209; 544/212; 544/113; 544/198; 540/599; 540/525
[58] Field of Search ............... 540/599, 575; 544/207, 544/209, 212, 113, 198

[56] References Cited

U.S. PATENT DOCUMENTS

| 4,086,204 | 4/1978 | Cassandrini et al. | 524/100 |
|---|---|---|---|
| 4,315,859 | 2/1982 | Nikles | 544/113 |
| 4,331,586 | 5/1982 | Hardy | 544/113 |
| 4,335,242 | 6/1982 | Wiezer et al. | 544/198 |
| 4,459,395 | 7/1984 | Cantatore | 544/198 |
| 4,477,615 | 10/1984 | Raspanti et al. | 524/100 |
| 4,547,548 | 10/1985 | Cantatore | 525/186 |
| 4,883,831 | 11/1989 | Nelson et al. | 524/100 |
| 4,883,860 | 11/1989 | Nelson et al. | 524/198 |
| 5,047,531 | 9/1991 | Cantatore et al. | 544/198 |

FOREIGN PATENT DOCUMENTS

| 904401 | 6/1964 | Belgium . |
|---|---|---|
| 0094048 | 11/1983 | European Pat. Off. . |
| 0117229 | 8/1984 | European Pat. Off. . |
| 0274764 | 7/1988 | European Pat. Off. . |
| 0314472 | 5/1989 | European Pat. Off. . |
| 0354184 | 2/1990 | European Pat. Off. . |
| 0354185 | 2/1990 | European Pat. Off. . |
| 0377324 | 7/1990 | European Pat. Off. . |
| 0389428 | 9/1990 | European Pat. Off. . |
| 0427674 | 5/1991 | European Pat. Off. . |
| 0357223 | 9/1991 | European Pat. Off. . |
| 63-196654 | 8/1988 | Japan . |
| 2143538 | 2/1985 | United Kingdom . |

OTHER PUBLICATIONS

C.A. 115, 10159r, Nelson et al, (1991).
C.A. 112, 199959d, Nelson et al, (1990).
C.A. 112, 199960x, Nelson et al (1990).
C.A. 114, 230088m, Nelson et al, (1991).
C.A. 111, 196078j, Toda et al (1989).
C.A. 110, 154268v, Bondarev et al (1989).
Akad. Nauk SSSR, Ser. Khim, 1988(7), p. 1640, Bondarev.
C.A. 105, 209942q Raspanti et al (1986).
Derwent 86-189962/30 (1986) Abstract.
C.A. 100, 157196z, Minagawa (1984).
Cantatore et al., Chemical Abstracts, vol. 113, entry 79797y (1990).
Cantatore et al., Chemical Abstracts, vol. 113, entry 60650y (1990).

Primary Examiner—John M. Ford
Attorney, Agent, or Firm—Luther A. R. Hall

[57] ABSTRACT

Compounds of formula I

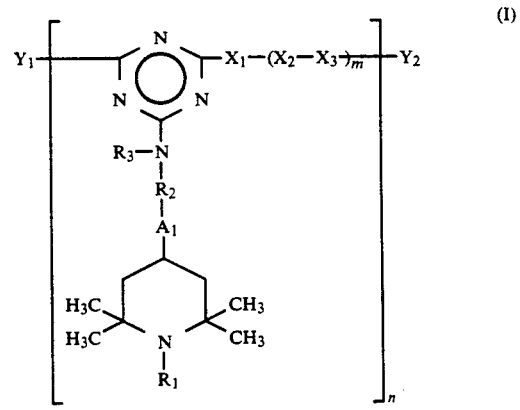

wherein $R_1$ is hydrogen, alkyl or alkoxy, $-A_1-R_2-N(R_3)-$ and $-X_1-(X_2-X_3)_m-$ are selected linking groups, $Y_1$ and $Y_2$ are selected terminal moieties and n is 1 to 50, are effective light, heat and oxidation stabilizers for a variety of organic materials.

8 Claims, No Drawings

PIPERIDINE-TRIAZINE COMPOUNDS

The present invention relates to novel piperidine-triazine compounds, to their use as light stabilisers, heat stabilisers and oxidation stabilisers for organic materials, in particular synthetic polymers, and to the organic materials thus stabilised.

It is known that synthetic polymers undergo a progressive change in physical properties, such as loss of mechanical strength and colour changes, when they are exposed to the action of sunlight or other sources of ultraviolet light in the presence of oxygen.

To retard the detrimental effect of ultraviolet radiation on synthetic polymers, additives having photostabilising properties are used, such as certain derivatives of benzophenone and benzotriazole, nickel complexes, alkylidenemalonates, cyanoacrylates, aromatic oxamides or sterically hindered amines.

Some triazine oligomers containing 2,2,6,6-tetramethylpiperidyl groups and their use as stabilisers for synthetic polymers have been reported in U.S. Pat. Nos. 4,086,204, 4,315,859, 4,331,586, 4,335,242, 4,459,395, 4,477,615 and 4,547,548, and European Laid Open Prints 117,229 and 354,185 and in Japanese Laid Open Print Sho 63-196,654.

The present invention relates to novel piperidine-triazine compounds of the formula (I)

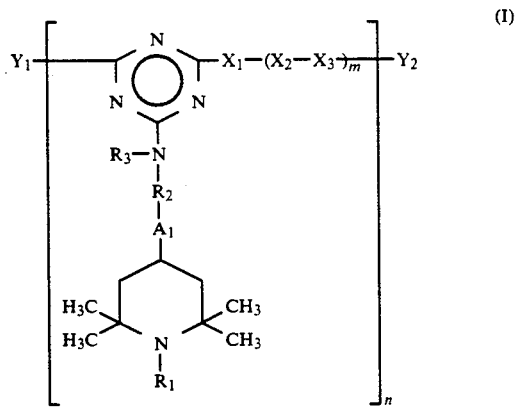

in which $R_1$ is hydrogen, $C_1$-$C_8$alkyl, O, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di- or tri-substituted on the phenyl by $C_1$-$C_4$alkyl; or $C_1$-$C_8$acyl, $A_1$ is —O— or >N—$R_4$ where $R_4$ is methyl, $C_1$-$C_8$acyl or ($C_1$-$C_8$alkoxy)-carbonyl, $R_2$ is $C_2$-$C_{12}$alkylene, $R_3$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; or a group of the formula (II)

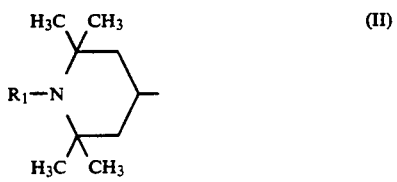

with $R_1$ being as defined above, or —$A_1$—$R_2$— is a direct bond and, in this case, $R_3$ is a group of the formula (III)

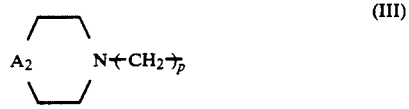

in which $A_2$ is a direct bond, —O—, —$CH_2$—, —$CH_2CH_2$— or >N—$CH_3$ and p is an integer from 2 to 6, or

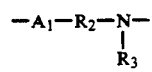

is also one of the groups of the formulae (IVa)-(IVd)

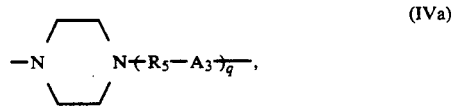

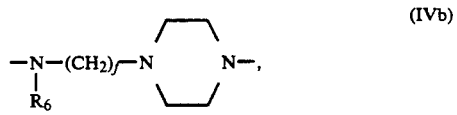

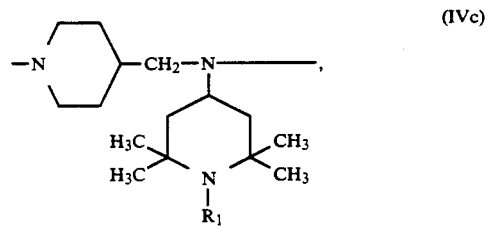

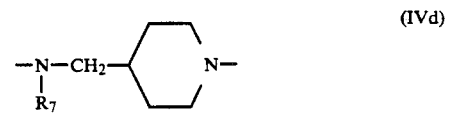

in which $R_5$ is $C_2$-$C_6$ alkylene, $A_3$ is —O— or a group >N—$R_8$ where $R_8$ is as defined for $R_3$, q is zero or 1, $R_6$ and $R_7$ are as defined for $R_4$, r is an integer from 2 to 6 and $R_1$ is as defined above, $X_1$ and $X_3$ which can be identical or different are one of the groups of the formulae (Va)-(Ve)

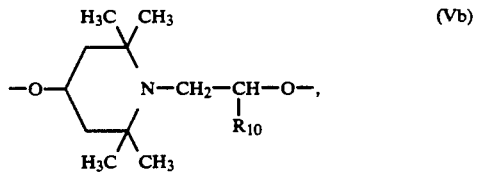

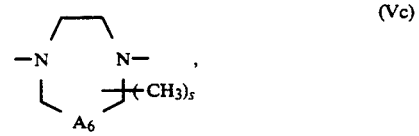

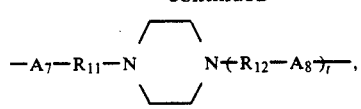 (Vd)

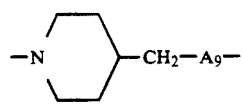 (Ve)

in which $A_4$, $A_5$, $A_7$, $A_8$ and $A_9$ which can be identical or different are as defined for $A_3$, $R_9$ is $C_2$-$C_{12}$alkylene, $C_4$-$C_{12}$alkylene interrupted by 1, 2 or 3 oxygen atoms or by 1 to 2 >N—$R_{13}$ groups where $R_{13}$ is as defined for $R_3$ or is $C_1$-$C_8$acyl or ($C_1$-$C_8$alkoxy)-carbonyl; $C_5$-$C_7$-cycloalkylene unsubstituted or mono-substituted by $C_1$-$C_4$alkyl, $C_5$-$C_7$cycloalkylene-di-($C_1$-$C_4$alkylene), $C_1$-$C_4$alkylene-di-($C_5$-$C_7$cycloalkylene), $C_2$-$C_4$alkylidene-di-($C_5$-$C_4$cycloalkylene), phenylene, phenylene-di-($C_1$-$C_4$alkylene), ($C_1$-$C_4$alkylene)-diphenylene or ($C_2$-$C_4$alkylidene)-diphenylene, where each phenylene group is unsubstituted or mono- or di-substituted by $C_1$-$C_4$alkyl, $R_{10}$ is hydrogen, $C_1$-$C_8$alkyl or phenyl, $A_6$ is a direct bond or —$CH_2$—, s is zero, 1, 2 or 3, $R_{11}$ and $R_{12}$ which can be identical or different are $C_2$-$C_6$alkylene and t is zero or 1, $X_2$ is $C_2$-$C_{12}$alkylene, $C_4$-$C_{12}$alkylene interrupted by 1, 2 or 3 oxygen atoms; 2-hydroxytrimethylene, xylylene, carbonyl or one of the groups of the formulae (VIa)–(VIe)

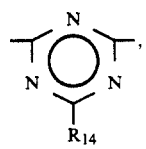 (VIa)

—CO—$R_{15}$—CO—, (VIb)

—COO—$R_{16}$—OOC—, (VIc)

—($CH_2$)$_u$—CO—, (VId)

—CONH—$R_{17}$—NHCO— (VIe)

in which $R_{14}$ is a group of the formula (VII)

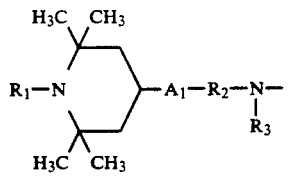 (VII)

in which $R_1$, $A_1$, $R_2$ and $R_3$ are as defined above, or $R_{14}$ is a group —$OR_{18}$, —$SR_{18}$ or

in which $R_{18}$, $R_{19}$ and $R_{20}$ which can be identical or different are hydrogen, $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; $C_7$-$C_9$phenylalkyl which is unsubstituted or mono-, di- or tri-substituted on the phenyl by $C_1$-$C_4$alkyl; tetrahydrofurfuryl, a group of the formula (II), $C_2$-$C_4$alkyl substituted in the 2-, 3- or 4-position by $C_1$-$C_8$alkoxy or by di-($C_1$-$C_4$alkyl)-amino or by a group of the formula (III); or the group

is a 5-membered to 7-membered heterocyclic group, $R_{15}$ is a direct bond, $C_1$-$C_{12}$alkylene, cyclohexylene, methylcyclohexylene or phenylene, $R_{16}$ is as defined for $R_9$, u is an integer from 1 to 10 and $R_{17}$ is as defined for $R_9$ or is a group

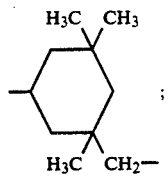

m is zero, 1, 2, 3 or 4, n is a number from 1 to 50, $Y_1$ and $Y_2$ are end groups which can have various definitions according to the type and molar ratios of the reagents used in the preparation. In particular, $Y_1$ can be Cl, OH, ONa, OK, a group $R_{14}$ or a group —$X_1Z$ or —$X_3Z$, where Z is hydrogen, methyl, benzyl, $C_1$-$C_8$ acyl or ($C_1$-$C_8$alkoxy)-carbonyl and $Y_2$ can be Z, a group

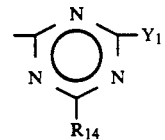

or a group —$X_2OH$. If m is zero and n is 1, the only definition of $Y_1$ is the group —$X_1Z$, with the proviso that the said group —$X_1Z$ is other than the group of the formula

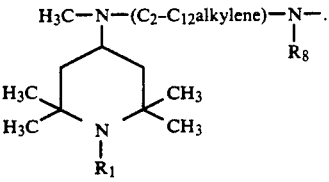

In the individual recurrent structural units of the formula (I), each of the groups $R_1$, $A_1$, $R_2$, $R_3$, $X_1$, $X_2$, $X_3$ and m can have the same or different definitions.

Examples of alkyl having up to 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

Examples of $C_2$-$C_4$alkyl substituted by $C_1$-$C_8$alkoxy, preferably by $C_1$-$C_4$alkoxy, especially methoxy or ethoxy, are 2-methoxyethyl, 2-ethoxyethyl, 3-methoxypropyl, 3-ethoxypropyl, 3-butoxypropyl, 3-octoxypropyl and 4-methoxybutyl.

Examples of $C_2$-$C_4$alkyl substituted by di-($C_1$-$C_4$alkyl)-amino, preferably by dimethylamino or diethylamino, are 2-dimethylaminoethyl, 2-diethylaminoethyl, 3-dimethylaminopropyl, 3-diethylaminopropyl, 3-dibutylaminopropyl and 4-diethylaminobutyl.

Examples of alkoxy having up to 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred examples of $R_1$ are $C_6$-$C_{12}$alkoxy, in particular heptoxy and octoxy.

Representative examples of the various $C_5$-$C_{12}$cycloalkyl substituents which are unsubstituted or mono-, di- or tri-substituted by $C_1$-$C_4$alkyl, are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or $C_1$-$C_4$alkyl-substituted cyclohexyl is preferred.

Representative examples of $C_5$-$C_{12}$cycloalkoxy $R_1$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having up to 18 carbon atoms are allyl, 2-methylallyl, hexenyl, decenyl, undecenyl and oleyl. Those alkenyl groups are preferred in which the carbon atom in the 1-position is saturated; allyl is particularly preferred.

Examples of substituted phenyl are methylphenyl, dimethylphenyl, trimethylphenyl, t-butylphenyl, di-t-butylphenyl, 3,5-di-t-butyl-4-methylphenyl, methoxyphenyl and ethoxyphenyl.

Representative examples of the various $C_7$-$C_9$phenylalkyl substituents which are unsubstituted or mono-, di- or tri-substituted on the phenyl by $C_1$-$C_4$alkyl, are benzyl, methylbenzyl, dimethylbenzyl, trimethylbenzyl, t-butylbenzyl and 2-phenylethyl. Benzyl is preferred.

Acyl $R_1$, $R_4$, $R_{13}$ and Z having up to 8 carbon atoms can be an aliphatic or aromatic group. Representative examples are formyl, acetyl, propionyl, butyryl, pentanoyl, hexanoyl, heptanoyl, octanoyl, benzoyl, acryloyl or crotonyl. $C_1$-$C_8$alkanoyl, $C_3$-$C_8$alkenoyl and benzoyl are preferred. Acetyl is especially preferred.

The 5- to 7-membered heterocyclic group

can contain a further hetero atom, for example nitrogen or oxygen; representative examples are 1-pyrrolidyl, 1-piperidyl, 4-morpholinyl, 4-methyl-1-piperazinyl and 1-hexahydroazepinyl. 4-Morpholinyl is preferred.

Examples of alkylene having up to 12 carbon atoms are methylene, ethylene, propylene, trimethylene, tetramethylene, pentamethylene, 2,2-dimethyltrimethylene, hexamethylene, trimethylhexamethylene, octamethylene, decamethylene and dodecamethylene.

Examples of $C_4$-$C_{12}$alkylene interrupted by 1, 2 or 3 oxygen atoms are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl and 3,6,9-trioxaundecane-1,11-diyl.

Representative examples of $C_4$-$C_{12}$alkylene $R_9$, $R_{16}$ and $R_{17}$ interrupted by 1 or $2 > N$—$R_{13}$ groups are the groups

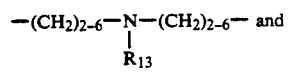

-continued

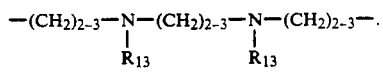

Representative examples of unsubstituted or substituted $C_5$-$C_7$-cycloalkylene and the groups containing 1 or 2 $C_5$-$C_7$cycloalkylene residues are cyclohexylene, methylcyclohexylene, cyclohexylenedimethylene, methylenedicyclohexylene and isopropylidenedicyclohexylene.

Representative examples of groups containing 1 or 2 unsubstituted or substituted phenylene groups are phenylene, methylphenylene, dimethylphenylene, xylylene, methylxylylene, methylenediphenylene and isopropylidenediphenylene.

Representative examples of ($C_1$-$C_8$alkoxy)-carbonyl are methoxycarbonyl, ethoxycarbonyl, propoxycarbonyl, butoxycarbonyl, pentoxycarbonyl, hexoxycarbonyl, heptoxycarbonyl and octoxycarbonyl.

The preferred definitions of $R_1$ are hydrogen, $C_1$-$C_4$alkyl, OH, $C_6$-$C_{12}$alkoxy, $C_5$-$C_8$cycloalkoxy, allyl, benzyl or acetyl, in particular hydrogen or methyl.

Those compounds of the formula (I) are preferred in which $A_1$ is —O— or $>N$—$R_4$, where $R_4$ is methyl, $C_1$-$C_6$acyl or ($C_1$-$C_6$alkoxy)-carbonyl, $R_2$ is $C_2$-$C_{10}$alkylene, $R_3$ is hydrogen, $C_1$-$C_{12}$alkyl, $C_5$-$C_8$cycloalkyl which is unsubstituted or mono-, di- or tri-substituted by $C_1$-$C_4$alkyl; benzyl which is unsubstituted or mono-, di- or tri-substituted on the phenyl by $C_1$-$C_4$alkyl; or a group of the formula (II), or —$A_1$—$R_2$— is a direct bond and, in this case, $R_3$ is a group of the formula (III) in which $A_2$ is a direct bond, —O— or —$CH_2$— and p is an integer from 2 to 4, or

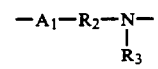

can also be one of the groups of the formulae (IVa)-(IVd) in which $R_5$ is $C_2$-$C_4$alkylene, $A_3$ is —O— or an $>N$—$R_8$ group where $R_8$ is as defined for $R_3$, q is zero or 1, $R_6$ and $R_7$ are as defined for $R_4$, r is an integer from 2 to 4, $X_1$ and $X_3$ which can be identical or different are one of the groups of the formulae (Va)-(Ve) in which $A_4$, $A_5$, $A_7$, $A_8$ and $A_9$ which can be identical or different are as defined for $A_3$, $R_9$ is $C_2$-$C_{10}$alkylene, $C_4$-$C_{10}$alkylene interrupted by 1, 2 or 3 oxygen atoms or by 1 or $2>N$—$R_{13}$ groups where $R_{13}$ is as defined for $R_3$ or is $C_1$-$C_4$ acyl or ($C_1$-$C_4$alkoxy)-carbonyl; cyclohexylene, cyclohexylenedimethylene, methylenedicyclohexylene, isopropylidenedicyclohexylene, phenylene, methylphenylene, xylylene, methylenediphenylene or isopropylidenediphenylene, $R_{10}$ is hydrogen, $C_1$-$C_4$alkyl or phenyl, $A_6$ is a direct bond or —$CH_2$—, s is zero, 1, 2 or 3, $R_{11}$ and $R_{12}$ which can be identical or different are $C_2$-$C_4$alkylene and t is zero or 1, $X_2$ is $C_2$-$C_{10}$alkylene, $C_4$-$C_{10}$alkylene interrupted by 1, 2 or 3 oxygen atoms; 2-hydroxytrimethylene, xylylene or one of the groups of the formulae (VIa)-(VIe) in which $R_{14}$ is a group of the formula (VII) or a group —$OR_{18}$, —$SR_{18}$ or

in which $R_{18}$, $R_{19}$ and $R_{20}$ which can be identical or different are hydrogen, $C_1$-$C_{12}$alkyl, $C_5$-$C_8$cycloalkyl which is unsubstituted or mono-, di-or tri-substituted by $C_1$-$C_4$alkyl; $C_3$-$C_{12}$alkenyl, phenyl which is unsubstituted or mono-, di- or trisubstituted by $C_1$-$C_4$alkyl or $C_1$-$C_4$alkoxy; benzyl which is unsubstituted or mono-, di- or tri-substituted on the phenyl by $C_1$-$C_4$alkyl; tetrahydrofurfuryl, a group of the formula (II), $C_2$-$C_3$alkyl substituted in the 2- or 3-position by $C_1$-$C_4$alkoxy or by di-($C_1$-$C_4$alkyl)-amino or by a group of the formula (III); or the group

is 1-pyrrolidyl, 1-piperidyl, 4-morpholinyl, 4-methyl-1-piperazinyl or 1-hexahydroazepinyl, $R_{15}$ is a direct bond, $C_1$-$C_{10}$alkylene, cyclohexylene or phenylene, $R_{16}$ is as defined for $R_9$, u is an integer from 1 to 5, $R_{17}$ is as defined for $R_9$ or is a group

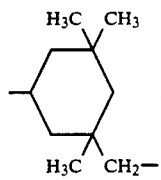

m is zero, 1, 2 or 3, n is a number from 1 to 30, $Y_1$ is Cl, OH, ONa, OK, a group $R_{14}$ or a group —$X_1Z$ or —$X_3Z$, where Z is hydrogen, methyl, benzyl, $C_1$-$C_4$acyl or ($C_1$-$C_4$alkoxy)-carbonyl, and $Y_2$ is Z, a group

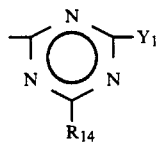

or a group —$X_2OH$.

Those compounds of the formula (I) are particularly preferred in which $A_1$ is —O— or >N—$R_4$, is methyl, $C_1$-$C_4$acyl or ($C_1$-$C_4$alkoxy)-carbonyl, $R_2$ is $C_2$-$C_8$alkylene, $R_3$ is hydrogen, $C_1$-$C_8$alkyl, cyclohexyl which is unsubstituted or mono-, di- or tri-substituted by $C_1$-$C_4$alkyl; benzyl or a group of the formula (II), or —$A_1$—$R_2$— is a direct bond and, in this case, $R_3$ is a group of the formula (III) in which $A_2$ is —O— or —$CH_2$— and p is 2 or 3, or

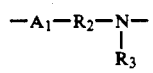

can also be one of the groups of the formulae (IVa)–(IVd) in which $R_5$ is $C_2$-$C_3$alkylene, $A_3$ is —O— or an >N—$R_8$ group where $R_8$ is as defined for $R_3$, q is zero or 1, $R_6$ and $R_7$ are as defined for $R_4$, r is 2 or 3, $X_1$ and $X_3$ which can be identical or different are one of the groups of the formulae (Va)-(Ve) in which $A_4$, $A_5$, $A_7$, $A_8$ and $A_9$ which can be identical or different are as defined for $A_3$, $R_9$ is $C_2$-$C_8$alkylene, $C_4$-$C_{10}$alkylene interrupted by 1, 2 or 3 oxygen atoms or by an >N—$R_{13}$ group with $R_{13}$ being hydrogen, methyl, acetyl or ($C_1$-$C_2$alkoxy)-carbonyl; cyclohexylene, cyclohexylenedimethylene, methylenedicyclohexylene, xylylene or isopropylidenediphenylene, $R_{10}$ is hydrogen, methyl or phenyl, $A_6$ is a direct bond or —$CH_2$—, s is zero, 1, 2 or 3, $R_{11}$ and $R_{12}$ which can be identical or different are $C_2$-$C_3$alkylene and t is zero or 1, $X_2$ is $C_2$-$C_8$alkylene, $C_4$-$C_8$alkylene interrupted by 1 or 2 oxygen atoms; 2-hydroxytrimethylene, xylylene or one of the groups of the formulae (VIa)–(VIe) in which $R_{14}$ is a group of the formula (VII) or a group —$OR_{18}$, —$SR_{18}$ or

where $R_{18}$, $R_{19}$ and $R_{20}$ which can be identical or different are hydrogen, $C_1$-$C_8$alkyl, cyclohexyl which is unsubstituted or mono-, di- or tri-substituted by $C_1$-$C_4$alkyl; allyl, undecenyl, phenyl, benzyl, tetrahydrofurfuryl, a group of the formula (II), $C_2$-$C_3$-alkyl substituted in the 2- or 3-position by $C_1$-$C_4$alkoxy, by dimethylamino or by diethylamino or by a group of the formula (III); or the group

is 4-morpholinyl, $R_{15}$ is a direct bond, $C_1$-$C_8$alkylene, cyclohexylene or phenylene, $R_{16}$ is $C_2$-$C_8$alkylene, $C_4$-$C_{10}$alkylene interrupted by 1, 2 or 3 oxygen atoms; cyclohexylenedimethylene, isopropylidenedicyclohexylene or isopropylidenediphenylene, u is an integer from 1 to 4, $R_{17}$ is as defined for $R_9$ or is methylphenylene, methylenediphenylene or a group

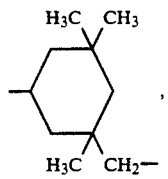

m is zero, 1, 2 or 3, n is a number from 1 to 20, $Y_1$ is OH, ONa, OK, a group $R_{14}$ or a group —$X_1Z$ or —$X_3Z$ where Z is hydrogen, methyl, acetyl or ($C_1$-$C_2$alkoxy)-carbonyl and $Y_2$ is Z, a group

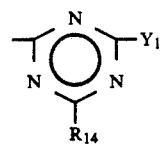

or a group —$X_2OH$.

Those compounds of the formula (I) are of special interest in which $A_1$ is —O— or >N—$R_4$, where $R_4$ is methyl, acetyl or ($C_1$-$C_2$alkoxy)-carbonyl, $R_2$ is $C_2$-$C_6$alkylene, $R_3$ is hydrogen, $C_1$-$C_4$alkyl, cyclohexyl, benzyl or a group of the formula (II), or —$A_1$—$R_2$— is a direct bond and, in this case, $R_3$ is a group of the formula (III) in which $A_2$ is —O— and p is 2 or 3, or

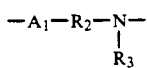

can also be one of the groups of the formulae (IVa)–(IVd) in which $R_5$ is $C_2$-$C_3$alkylene, $A_3$ is —O— or an $>N$—$R_8$ group where $R_8$ is as defined for $R_3$, q is zero or 1, $R_6$ and $R_7$ are as defined for $R_4$, r is 2 or 3, $X_1$ and $X_3$ which can be identical or different are one of the groups of the formulae (Va)–(Ve) in which $A_4$, $A_5$, $A_7$, $A_8$ and $A_9$ which can be identical or different are as defined for $A_3$, $R_9$ is $C_2$-$C_6$alkylene, $C_6$-$C_{10}$alkylene interrupted by 2 or 3 oxygen atoms; cyclohexylenedimethylene, methylenedicyclohexylene or xylylene, $R_{10}$ is hydrogen or methyl, $A_6$ is a direct bond, s is zero or 1, $R_{11}$ and $R_{12}$ are ethylene or trimethylene and t is zero or 1, $X_2$ is $C_2$-$C_6$alkylene, 2-hydroxytrimethylene, xylylene or one of the groups of the formulae (VIa)–(VIe) in which $R_{14}$ is a group of the formula (VII) or a group —$OR_{18}$ or

in which $R_{18}$ is $C_1$-$C_4$alkyl, cyclohexyl, allyl, phenyl, benzyl, tetrahydrofurfuryl or a group of the formula (II), $R_{19}$ and $R_{20}$ which can be identical or different are as defined above for $R_{18}$ or are hydrogen or $C_2$-$C_3$alkyl substituted in the 2- or 3-position by methoxy, by ethoxy, by dimethylamino or by diethylamino or by a group of the formula (III); or the group

is 4-morpholinyl, $R_{15}$ is a direct bond or $C_1$-$C_8$alkylene, $R_{16}$ is $C_4$-$C_6$alkylene, u is 1 or 2, $R_{17}$ is $C_2$-$C_6$alkylene or a group

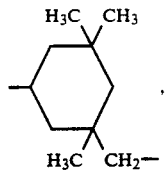

m is zero, 1 or 2, n is a number from 1 to 15, $Y_1$ is OH, ONa, OK, a group $R_{14}$ or a group —$X_1Z$ or —$X_3Z$ where Z is hydrogen, methyl, acetyl or ($C_1$-$C_2$alkoxy)-carbonyl and $Y_2$ is Z, a group

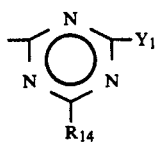

or a group —$X_2OH$.

Those compounds of the formula (I) are of particular interest in which $R_1$ is hydrogen or methyl, $A_1$ is —O— or $>N$—$CH_3$, $R_2$ is —$(CH_2)_{2-6}$—, $R_3$ is hydrogen, methyl, 2,2,6,6-tetramethyl-4-piperidyl or 1,2,2,6,6-pentamethyl-4-piperidyl, or —$A_1$—$R_2$— is a direct bond and, in this case, $R_3$ is a group

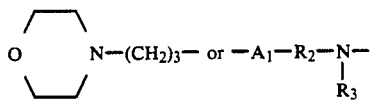

can also be one of the groups of the formulae (IVa)–(IVc) in which $R_5$ is ethylene, $A_3$ is —O— or $>N$—$R_8$, where $R_8$ is as defined for $R_3$, q is zero or 1, $R_6$ is methyl, r is 2, $X_1$ and $X_3$ which can be identical or different are a group of the formula (Va) or (Vb) in which $A_4$ and $A_5$ which can be identical or different are an $>N$—$R_8$ group where $R_8$ is as defined for $R_3$, $R_9$ is —$(CH_2)_{2-6}$— or —$(CH_2)_3$—O—$(CH_2)_{2-4}$—O—$(CH_2)_3$— and $R_{10}$ is hydrogen or methyl, $X_2$ is 2-hydroxytrimethylene or a group of the formula (VIa) where $R_{14}$ is a group of the formula (VII), m is zero or 1, n is a number from 1 to 10, $Y_1$ is OH, ONa, OK, a group $R_{14}$ or a group —$X_1Z$ or —$X_3Z$ with Z being hydrogen or methyl and $Y_2$ is hydrogen, methyl or a group

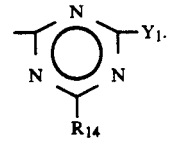

Those compounds of the formula (I) are also of particular interest, in which $R_1$ is hydrogen or methyl, $A_1$ is $>N$—$CH_3$, $R_2$ is —$(CH_2)_{2-6}$—, $R_3$ is 2,2,6,6-tetramethyl-4-piperidyl or 1,2,2,6,6-pentamethyl-4-piperidyl, or —$A_1$—$R_2$— is a direct bond and, in this case, $R_3$ is a group

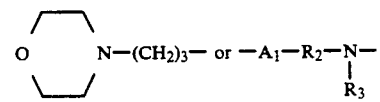

is a group of the formula (IVa) or (IVc), q and m are zero, $X_1$ is a group of the formula (Va) in which $A_4$ and $A_5$ which are identical or different are an $>N$—$R_8$ group where $R_8$ is hydrogen, 2,2,6,6-tetramethyl-4-piperidyl or 1,2,2,6,6-pentamethyl-4-piperidyl, $R_9$ is —$(CH_2)_{2-6}$— and n is a number from 1 to 10.

The compounds of the present invention can be prepared by processes known per se, for example as described in U.S. Pat. Nos. 4,086,204, 4,459,395 and 4,547,548, by reacting, in any order, and in the appropriate molar ratios, e.g. stoichiometric ratios, cyanuric chloride with compounds of the formulae (VIIIa), (VIIIb), (VIIIc) and (VIIId)

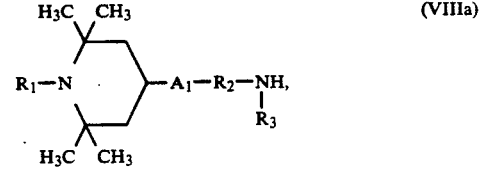

(VIIIa)

-continued $$H-X_3-H \qquad (VIIId)$$

in which $R_1$, $A_1$, $R_2$, $R_3$, $X_1$, $X_2$ and $X_3$ are as defined above and $D_1$ and $D_2$ are e.g. Cl, Br, methoxy or ethoxy or $D_1-X_2-D_2$ is epichlorohydrin or a diisocyanate $OCN-R_{17}-NCO$ with $R_{17}$ being as defined above.

The compounds of the formula (VIIIa) can be prepared by known processes, starting from 2,2,6,6-tetramethyl-4-piperidone or derivatives thereof.

The intermediates of the formula (VIIIa) which corresponds to

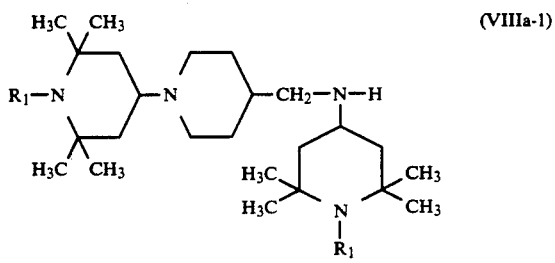

(VIIIa-1)

wherein $R_1$ is hydrogen, $C_1-C_8$alkyl, O·, OH, NO, $CH_2CN$, $C_1-C_{18}$alkoxy, $C_5-C_{12}$cycloalkoxy, $C_3-C_6$alkenyl, $C_7-C_9$phenylalkyl unsubstituted or substituted on the phenyl radical by 1, 2 or 3 $C_1-C_4$alkyl; or is $C_1-C_8$acyl, are new and also possess stabilising effectiveness.

The compounds of the formulae (VIIIb), (VIIIc) and (VIIId) are commercially available or can easily be prepared by known processes.

As mentioned at the outset, the novel compounds of the present invention are highly effective in improving the light stability, heat stability and oxidation stability of organic materials, in particular synthetic polymers and copolymers.

Examples of such organic materials which can be stabilised are:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefines and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate copolymers and their copolymers with carbon monoxide or ethylene/acrylic acid copolymers and their salts (ionomers) and terpolymers of ethylene with propylene and a diene, such as hexadiene, dicyclopentadiene or ethylidene-norbornene; as well as mixtures of such copolymers and their mixtures with polymers mentioned in 1) above, for example polypropylene/ethylene-propylene-copolymers, LDPE/ethylene-vinyl acetate copolymers (EVA), LDPE/ethylene-acrylic acid copolymers (EAA), LLDPE/EVA, LLDPE/EAA and statistical or alternating polyalkylene/carbon monoxide-copolymers as well as their mixtures with other polymers, for example polyamide.

3a. Hydrocarbon resins (for example $C_5-C_9$) and hydrogenated modifications thereof (for example tackyfiers) and mixtures of polyalkylenes and starch.

4. Polystyrene, poly-(p-methylstyrene), poly-($\alpha$-methylstyrene).

5. Copolymers of styrene or $\alpha$-methylstyrene with dienes or acrylic derivatives, such as, for example, styrene/butadiene, styrene/acrylonitrile, styrene/alkyl methacrylate, styrene/maleic anhydride, styrene/butadiene/alkyl acrylate, styrene/butadiene/alkyl methacrylate styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or $\alpha$-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymer, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, copolymers of ethylene and chlorinated ethylene, epichlorohydrin homo- and copolymers, polymers from halogen-containing vinyl compounds, as for example, poly- vinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, with butyl acrylate impact resistant modified polymethyl methacrylate, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12, 4/6, 12/12 polyamide 11, polyamide 12, aromatic polyamides obtained by condensation of m-xylene diamine and adipic acid; polyamides prepared from hexamethylenediamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamides with polyolefins, olefin copolymers, ionomers or chemically bonded or grafted elastomers; or with polyethers, such as for instance, with polyethylene glycols, polypropylene glycols or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and or from hydroxycarboxylic acids or the corresponding lactones, such as polyethylene terephthalate, polybutylene terephthalate, poly-1,4-dimethylolcyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates and polyester-carbonates.

19. Polysulfones, polyether-sulfones and polyether-ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymer-homologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/butadiene copolymers.

The compounds of the instant invention are particularly sutiable for improving the light stability, heat stability and oxidation stability of polyolefins, especially polyethylene and polypropylene.

The compounds of the instant invention can be used in mixtures with organic materials in various proportions depending on the nature of the material to be stabilised, on the end use and on the presence of other additives.

In general, it is appropriate to use, for example, 0.01 to 5% by weight of the compounds of the instant invention, relative to the weight of the material to be stabilised, preferably between 0.05 and 1%.

In general, the compounds of the instant invention can be added to the polymeric materials before, during or after the polymerisation or crosslinking of the said materials.

The compounds of the instant invention can be incorporated in the pure form or encapsulated in waxes, oils or polymers into the polymeric materials.

The compounds of the instant invention can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilised with the products of the instant invention can be used for the production of mouldings, films, tapes, monofilaments, fibres, surface coatings and the like.

If desired, other conventional additives for synthetic polymers, such as antioxidants, UV absorbers, nickel stabilisers, pigments, fillers, plasticisers, antistatic agents, flameproofing agents, lubricants, corrosion inhibitors and metal deactivators, can be added to the mixtures of the compounds of the instant invention with the organic materials.

Particular examples of additives which can be used in admixture with the compounds of the instant invention are:

1. Antioxidants 1.1. Alkylated monophenols, for example 2,6-di-tert-butyl-4-methyl-phenol, 2-tert-butyl-4,6-dimethylphenol, 2,6-di-tert-butyl-4-ethylphenol, 2,6-di-tert-butyl-4-n-butylphenol, 2,6-di-tert-butyl-4-iso-butylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexyl-phenol, 2,6-di-tert-butyl-4-methoxymethylphenol, 2,6-di-nonyl-4-methylphenol, 2,4-dimethyl-6-(1'-methyl-undec-1'-yl)-phenol, 2,4-dimethyl-6-(1'-methylheptadec-1'-yl)-phenol, 2,4-dimethyl-6-(1'methyl-tridec-1'-yl)-phenol and mixtures thereof.

1.2. Alkylthiomethylphenols, for example 2,4dioctylthiomethyl-6-tert-butylphenol, 2,4-dioctylthiomethyl-6-methylphenol, 2,4-dioctylthiomethyl-6-ethylphenol, 2,6-di-do-decylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-di-phenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl-stearate, bis-(3,5-di-tert-butyl-4-hydroxyphenyl)adipate.

1.4. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thio-bis(6-tert-butyl-2-methylphenol), 4,4'-thio-bis-(3,6-di-sec-amylphenol), 4,4'-bis-(2,6-dimethyl-4-hydroxyphenyl)-disulfide.

1.5. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylene-bis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis-(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butan, 2,2-bis-(3,5-di-tert.-butyl-4-hydroxyphenyl)-propan, 2,2-bis-(5-tert.-butyl-4-hydroxy-2-methylphenyl)-4-n-dodecylmercapto-butan, 1,1,5,5-tetra-(5-tert.-butyl-4-hydroxy-2-methylphenyl)-pentan.

1.6. O-, N- and S-benzyl compounds, for example 3,5,3',5'-tetra-tert.-butyl-4,4'-dihydroxydibenzylether, octadecyl-4-hydroxy-3,5-dimethylbenzyl-mercaptoacetate, tris-(3,5-di-tert.-butyl-4-hydroxybenzyl)-amine, bis-(4-tert.-butyl-3-hydroxy-2,6-dimethylbenzyl)-dithioterephthalate, bis-(3,5-di-tert.-butyl-4-hydroxybenzyl)-sulfide, isooctyl-3,5-di-tert.-butyl-4-hydroxybenzylmercaptoacetate.

1.7. Hydroxybenzylated Malonates, for example di-octadecyl-2,2-bis-(3,5-di-tert.-butyl-2-hydroxybenzyl)-malonate, di-octadecyl-2-(3-tert.-butyl-4-hydroxy-5-methylbenzyl)-malonate, di-dodecylmercaptoethyl-2,2-bis-(3,5-di-tert.-butyl-4-hydroxybenzyl)-malonate, Di-[4-(1,1,3,3-tetramethylbutyl)-phenyl]-2,2-bis-(3,5-di-tert.-butyl-4-hydroxybenzyl)-malonate.

1.8. Hydroxybenzyl-Aromatics, for example 1,3,5-tris-(3,5-di-tert.-butyl-4-hydroxybenzyl)-2,4,6-trimethylbenzene, 1,4-bis-(3,5-di-tert.-butyl-4-hydroxybenzyl)-2,3,5,6-tetramethylbenzene, 2,4,6-tris-(3,5-di-tert.-butyl-4-hydroxybenzyl)-phenol.

1.9. Triazine Compounds, for example 2,4-bis-octylmercapto-6-(3,5-di-tert.-butyl-4-hydroxyanilino)-1,3,5-triazine, 2-octylmercapto-4,6-bis-(3,5-di-tert.-butyl-4-hydroxyanilino)-1,3,5-triazine, 2-octylmercapto-4,6-bis-(3,5-di-tert.-butyl-4-hydroxyphenoxy)-1,3,5-triazine, 2,4,6-tris-(3,5-di-tert.-butyl-4-hydroxyphenoxy)-1,2,3-triazine, 1,3,5-tris-(3,5-di-tert.-butyl-4-hydroxybenzyl)-isocyanurate, 1,3,5-tris-(4-tert.-butyl-3-hydroxy-2,6-dimethylbenzyl)-isocyanurate, 2,4,6-tris-(3,5-di-tert.-butyl-4-hydroxyphenylethyl)-1,3,5-triazine, 1,3,5-tris-(3,5-di-tert.butyl-4-hydroxyphenylpropionyl)-hexahydro-1,3,5-triazine, 1,3,5-tris-(3,5-dicyclohexyl-4-hydroxybenzyl)-isocyanurate.

1.10. Benzylphosphonates, for example dimethyl-2,5-di-tert.-butyl-4-hydroxybenzylphosphonate, diethyl-3,5-di-tert.-butyl-4-hydroxybenzylphosphonate, dioctadecyl-3,5-di-tert.-butyl-4-hydroxybenzylphosphonate, dioctadecyl-5-tert.-butyl-4-hydroxy-3-methylbenzylphosphonate, Ca-salt of the 3,5-di-tert.-butyl-4-hydroxybenzyl-phosphonic acid monoethylester.

1.11. Acylaminophenols, for example lauric acid 4-hydroxyanilide, stearic acid 4-hydroxyanilide, octyl N-(3,5-di-tert-butyl-4-hydroxyphenyl)-carbamate.

1.12. Esters of $\beta$-(3,5-di-tert-butyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, tri-methylhexanediol, trimethylolpropane, 4-hydroxymethyl-1-phospha-2,6,7-trioxabicyclo[2.2.2]-octane.

1.13. Esters of $\beta$-(5-tert-butyl-4-hydroxy-3-methylphenyl)propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.14 Esters of $\beta$-(3,5-dicyclohexyl-4-hydroxyphenyl)-propionic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.15 Esters of 3,5-di-tert.-butyl-4-hydroxyphenyl acetic acid with mono- or polyhydric alcohols, e.g. with methanol, ethanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxalic acid diamide, 3-thiaundecanol, 3-thiapentadecanol, trimethylhexanediol, trimethylolpropane, 4-hydroxymethyl-1-phospha-2,6,7-trioxabicyclo-[2.2.2]-octane.

1.16. Amides of β-(3,5-di-tert-butyl-4-hydroxyphenyl)propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)-tri-methylene-diamine, N,N'-bis(3,5-di-tert-butyl-4-hydroxyphenylpropionyl)-hydrazine.

2. UV absorbers and light stabilisers 2.1.2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl), mixture of 5-chloro-3'-tert.-butyl-5'-(2-octyloxycarbonylethyl)-and 5-chloro-3'-tert.-butyl-5'-[2-(2-ethylhexyloxy)-carbonylethyl]-, 5-chloro-3'-tert.-butyl-5'-(2-methoxycarbonylethyl)-, 3'-tert.-butyl-5'-(2-methoxycarbonylethyl)-, 3'-tert.-butyl-5'-(2-octyloxycarbonylethyl)-, 3'-tert.-butyl-5'-[2-(2-ethyl-hexyloxy)carbonylethyl]-, 3'-dodecyl-5'-methyl- and 3'-tert.-butyl-5'-(2-isooctyloxycarbonylethyl)-2'-hydroxyphenyl-2H-benztriazole(2), 2,2'-methylene-bis[4-(1,1,3,3-tetramethylbutyl)-6-benztriazole-2-yl-phenol]; product of ester interchange of 2-[3'-tert.-butyl-5'-(2-methoxycarbonylethyl)-2'-hydroxy-phenyl]-2H-benztriazole with polyethylene glycol 300; [R—CH$_2$CH$_2$—COO(CH$_2$)$_3$]$_2$ with R = 3'-tert.-butyl-4'-hydroxy-5'-2H-benzotriazole-2-yl-phenyl.

2.2.2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tert.butylphenyl salicylate, phenyl salicylate, octylphenyl salicylate, dibenzoylresorcinol, bis-(4-tert.butylbenzoyl)-resorcinol, benzoylresorcinol, 2,4-di-tert.butylphenyl 3,5-di-tert.butyl-4-hydroxybenzoate, hexadecyl 3,5-di-tert.butyl-4-hydroxybenzoate, octadecyl 3,5-di-tert.-butyl-4-hydroxybenzoate, 2 methyl-4,6-di-tert.-butylphenyl 3,5-di-tert.-butyl-4-hydroxybenzoate.

2.4. Acrylates, for examples ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzyl-phosphonic acid monoalkyl esters, e.g. of the methyl or ethyl ester, nickel complexes of ketoximes, e.g. of 2-hydroxy-4-methyl-phenyl undecyl ketoxime, nickel complexes of 1-phenyl-4-lauroyl-5-hydroxypyrazole, with or without additional ligands.

2.6. Sterically hindered amines, for example bis(2,2,6,6-tetramethyl-piperidyl) sebacate, bis-(2,2,6,6-tetramethyl-piperidyl) succinate, bis(1,2,2,6,6-pentamethylpiperidyl) sebacate, bis(1,2,2,6,6-pentamethylpiperidyl) n-butyl-3,5-di-tert-butyl-4-hydroxy-benzylmalonate, the condensation product of 1-(2-hydroxyethyl)-2,2,6,6-tetramethyl-4-hydroxypiperidine and succinic acid, the condensation product of N,N'-bis(2,2,6,6-tetramethyl-4-piperidyl)-hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis-(3,3,5,5-tetramethylpiperazinone), 4-benzoyl-2,2,6,6-tetramethylpiperidine, 4-stearyloxy-2,2,6,6-tetramethylpiperidine, bis-(1,2,2,6,6-pentamethylpiperidyl)-2-n-butyl-2-(2-hydroxy-3,5-di-tert.-butylbenzyl) malonate, 3-n-octyl-7,7,9,9-tetramethyl-1,3,8-triazasprio[4.5]decan-2,4-dion, bis-(1-octyloxy-2,2,6,6-tetramethylpiperidyl) sebacate, bis-(1-octyloxy-2,2,6,6-tetramethylpiperidyl) succinate, product of condensation of N,N'-bis-(2,2,6,6-tetramethyl-4-piperidyl)-hexamethylene diamine and 4-morpholino-2,6-dichloro-1,3,5-triazine, product of condensation of-chloro-4,6-di-(4-n-butylamino-2,2,6,6-tetramethylpiperidyl)-1,3,5-triazine and 1,2-bis-(3-aminopropylamino)ethane, product of condensation of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dion, 3-dodecyl-1-(2,2,6,6-tetramethyl-4piperidyl)pyrrolidin-2,5-dion, 3-dodecyl-1-(1,2,2,6,6-pentamethyl-4-piperidyl)-pyrrolidin-2,5-dion.

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylamino-propyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2hydroxy-4-octyloxy-phenyl)-4,6-bis(2,4-dimethyl-phenyl)-1,3,5-triazine, 2-(2,4-dihydroxy-phenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethyl)-1,3,5-triazine, 2-[2-hydroxy-4(2-hydroxy-3-octyloxy-propyloxy)-phenyl]-4,6-bis(2,4-dimethyl)-1,3,5-triazine.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)-oxalodihydrazide, Oxanilide, isophthalic acid dihydrazide, sebacic acid-bis-phenylhydrazide, N,N'-diacetal-adipinic acid dihydrazide, N,N'-bis-salicyloyl-oxalic acid dihydrazide, N,N'-bis-salicyloyl-thiopropionic acid dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diiso- decyl pentaerythritol diphosphite, bis(2,4-di-tert.-butylphenyl) pentaerythritol diphosphite, bis-(2,6-di-tert.-butyl-4-methylphenyl)-pentaerythritol diphosphite, bis-isodecyloxy-pentaerythritol diphosphite, bis-(2,4-di-tert.-butyl-6-methylphenyl)-pentaerythritol diphosphite, bis-(2,4,6-tri-tert.-butylphenyl)-pentaerythritol diphsophite, tristearyl sorbitol triphosphite, tetrakis(2,4-di-tert-butylphenyl) 4,4'-biphenylene diphosphonite, 6-isooctyloxy-2,4,8,10-tetratert.-butyl-12H-dibenz[d,g]-1,3,2-dioxaphosphocin, 6-fluoro-2,4,8,10-tetra-tert.-butyl-12-methyl-dibenz[d,g]-1,3,2-dioxaphosphocin.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecyl-mercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg behenate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flame-proofing agents, antistatic agents and blowing agents.

The compounds of the invention can also be used as stabilisers, especially as light stabilisers, for almost all materials known in the art of photographic reproduction and other reproduction techniques as e.g. described in Research Disclosure 1990, 314 29 (pages 474 to 480).

Several examples of the preparation of the compounds of the formula (I) are reported for more detailed illustration of the present invention; these examples are given solely for illustrative purposes and do not imply any restriction. Particularly preferred compounds of the formula (I) are disclosed in the following examples 2, 3, 4, 7 and 8.

The number-average molecular weight given in the following examples is determined by the method described in EP-A-255,990, from page 18, line 54, to page 19, line 15.

EXAMPLE 1

A solution of 14.75 g (0.08 mol) of cyanuric chloride in 100 ml of xylene is added slowly to a solution of 29.33 g (0.08 mol) of N-methyl-N,N'-bis(2,2,6,6-tetramethyl-4-piperidyl)-1,3-propanediamine in 150 ml of xylene, maintaining the temperature at $-20°$ C. The mixture is stirred for 2 hours at $-20°$ C., 9.30 g (0.08 mol) of 1,6-hexanediamine are added and the mixture is heated for 2 hours at 60° C.; 19.39 g (0.16 mol) of 33% sodium hydroxide are added and the mixture is heated for 2 hours at 90° C. 6.4 g (0.6 mol) of ground sodium hydroxide are added and the mixture is heated under reflux to remove the water and part of the solvent in such a way that an internal temperature of 155° C. is reached after 6 hours, and this temperature is then maintained for 12 hours. After cooling to about 70° C. and dilution with 150 ml of xylene, the reaction mixture is filtered and evaporated under reduced pressure, which gives a compound having a melting point of 125°-135° C. and a molecular weight of $\overline{Mn}=4050$ and containing repetitive units of the formula

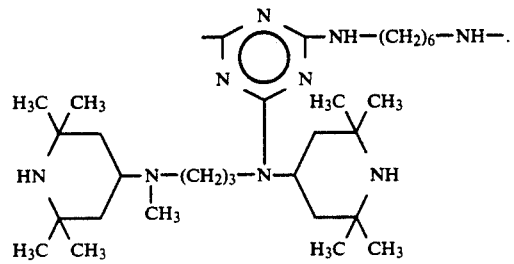

EXAMPLE 2

Following the procedure described in Example 1, but using 5.93 g (0.08 mol) of 1,3-propanediamine in place of the 1,6-hexanediamine, a compound having a melting point of 134°-139° C. and a molecular weight of $\overline{Mn}=2700$ and containing recurrent units of the formula

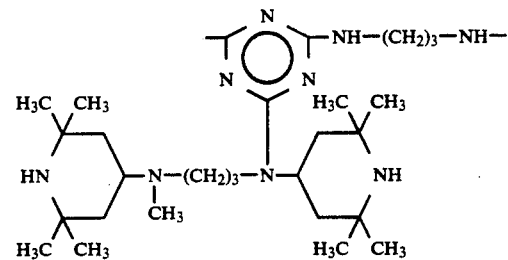

is obtained.

EXAMPLE 3

Following the procedure described in Example 1, but using 39.47 g (0.1 mol) of N,N'-bis(2,2,6,6-tetramethyl-4-piperidyl)-1,6-hexanediamine in place of the 1,6-hexanediamine, a compound having a melting point of 135°-139° C. and a molecular weight of $\overline{Mn}=3260$ and containing recurrent units of the formula

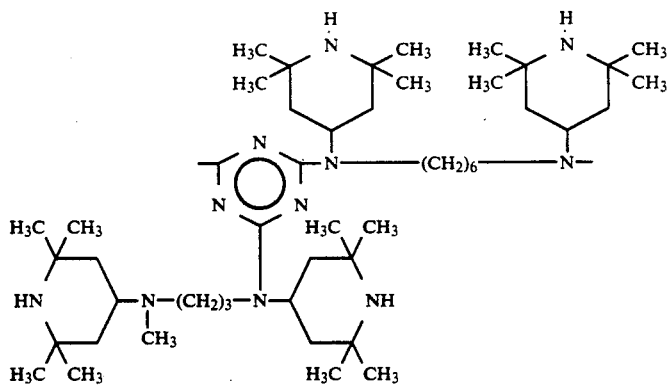

is obtained.

EXAMPLE 4

A solution of 18.44 g (0.1 mol) of cyanuric chloride in 180 ml of dichloromethane is added slowly to a solution of 28.34 g (0.1 mol) of N-(2,2,6,6-tetramethyl-4-piperidyl)-4-morpholinopropaneamine in 100 ml of dichloromethane, maintaining the temperature at −10° C.

After 1 hour at between −10° C. and 0° C., 12.12 g (0.1 mol) of 33% sodium hydroxide are slowly added, maintaining the temperature at 0° C., and the mixture is then stirred for 1 hour at between 0° C. and 20° C. 49.34 g (0.125 mol) of N,N'-bis(2,2,6,6-tetramethyl-4-piperidyl)-1,6-hexanediamine are added and the mixture is heated up to 60° C. to remove the dichloromethane; 150 ml of xylene are added and the mixture is heated for 2 hours at 60° C.

12 g (0.3 mol) of ground sodium hydroxide are added and the mixture is heated for 2 hours at 90° C. and then heated to reflux to remove the water and part of the solvent in such a way that an internal temperature of 155° C. is reached after 15 hours of refluxing, and this temperature is maintained for 2 hours. After cooling to ambient temperature and dilution with 150 ml of xylene, the reaction mixture is filtered and evaporated under reduced pressure.

This gives a compound having a melting point of 124°–127° C. and a molecular weight of $\overline{Mn}=2230$ and containing recurrent units of the formula

EXAMPLE 5

A) Preparation of N,1-bis(2,2,6,6-tetramethyl-4-piperidyl)-4-piperidinemethaneamine.

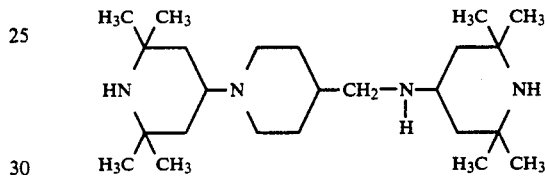

223.5 g (1.44 mol) of 2,2,6,6-tetramethyl-4-piperidone, 82.2 g (0.72 mol) of 4-piperidinemethaneamine, 0.2 g of benzoic acid and 500 ml of toluene are heated under reflux while separating the water by azeotropic distillation. The mixture is evaporated under reduced pressure and the residue is dissolved in 800 ml of methanol. 12 g of 5% Pt on carbon are added and hydrogenation is carried out at 40 bar and room temperature. The catalyst is then removed by filtration, the solvent is evaporated under reduced pressure and the residue is crystallized from acetonitrile. The product has a melting point of 91°–93° C.

B) Following the procedure described in Example 4, but using 39.27 g (0.1 mol) of N,1-bis(2,2,6,6-tetramethyl-4-piperidyl)-4-piperidinemethaneamine in place of the N-(2,2,6,6-tetramethyl-4-piperidyl)-4-morpholinopropaneamine, a compound having a melting point of 162°–164° C. and a molecular weight of $\overline{Mn}=2540$ and containing recurrent units of the formula

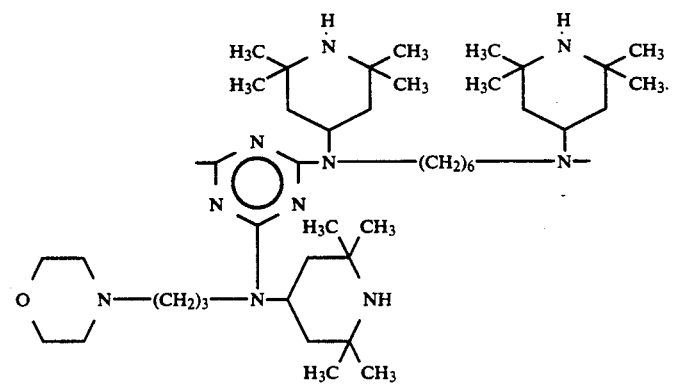

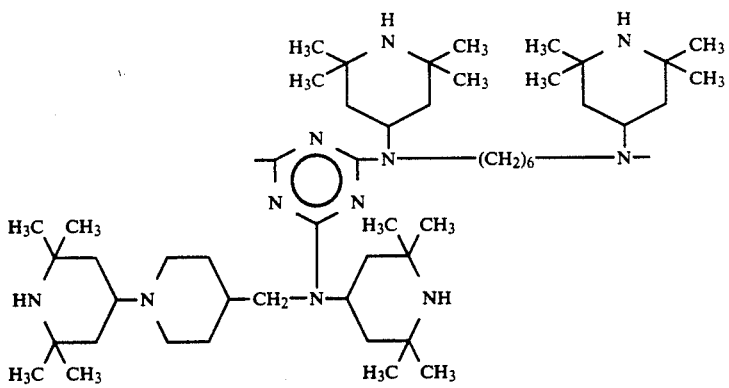

is obtained.

EXAMPLE 6

Following the procedure described in Example 4, but using 39.27 g (0.1 mol) of N,1-bis(2,2,6,6-tetramethyl-4-piperidyl)-4-piperidinemethaneamine and 6.01 g (0.1 mol) of 1,2-ethanediamine in place of N-(2,2,6,6-tetramethyl-4-piperidyl)-4-morpholinopropaneamine and N,N'-bis(2,2,6,6-tetramethyl-4-piperidyl)-1,6-hexanediamine respectively, a compound having a melting point of 208°–212° C. and a molecular weight of $\overline{Mn}=4000$ and containing recurrent units of the formula

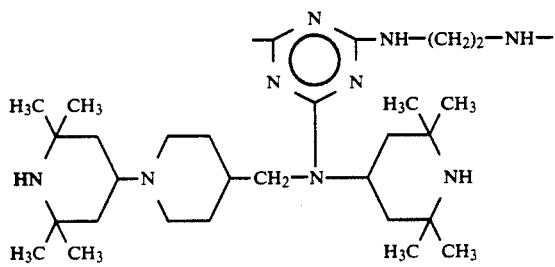

is obtained.

EXAMPLE 7

Following the procedure described in Example 4, but using 39.27 g (0.1 mol) of N,1-bis(2,2,6,6-tetramethyl-4-piperidyl)-4-piperidinemethaneamine and 9.63 g (0.13 mol) of 1,3-propanediamine in place of N-(2,2,6,6-tetramethyl-4-piperidyl)-4-morpholinopropaneamine and N,N'-bis(2,2,6,6-tetramethyl-4-piperidyl)-1,6-hexanediamine respectively, a compound having a melting point of 157°–158° C. and a molecular weight of $\overline{Mn}=1590$ and containing recurring units of the formula

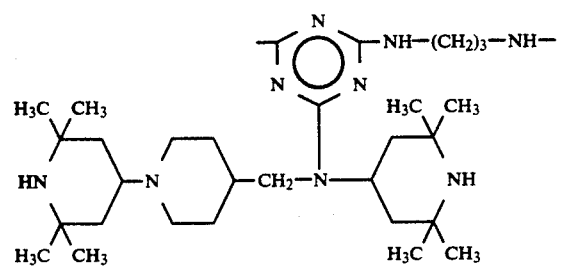

is obtained.

EXAMPLE 8

A solution of 19.73 g (0.05 mol) of N,N'-bis(2,2,6,6-tetramethyl-4-piperidyl)-1,6-hexanediamine in 70 ml of dichloromethane is added slowly to a solution of 18.44 g (0.1 mol) of cyanuric chloride in 180 ml of dichloromethane, maintaining the temperature at −10° C.

After 1 hour at between −10° C. and 0° C., 12.12 g (0.1 mol) of 33% sodium hydroxide are added slowly, maintaining the temperature at 0° C., and the mixture is then stirred for 1 hour at between 0° C. and 20° C. A solution of 25.92 g (0.115 mol) of 1-(2,2,6,6-tetramethyl-4-piperidyl)piperazine in 70 ml of dichloromethane is slowly added, maintaining the temperature at 20° C., and this mixture is stirred at this temperature for 4 hours.

It is then heated up to 60° C. to remove the dichloromethane, and 150 ml of xylene, 31.57 g (0.08 mol) of N,N'-bis(2,2,6,6-tetramethyl-4-piperidyl)-1,6-hexanediamine and 12 g (0.3 mol) of ground sodium hydroxide are then added and the mixture is heated under reflux to remove the water and part of the solvent in such a way that an internal temperature of 160° C. is reached after heating for 10 hours, and heating at this temperature is continued for 4 hours.

After cooling to about 70° C. and dilution with 150 ml of xylene, the reaction mixture is filtered and evaporated under reduced pressure. This gives a compound of melting point 143°–149° C. and a molecular weight of $\overline{Mn}=1900$ and containing recurrent units of the formula

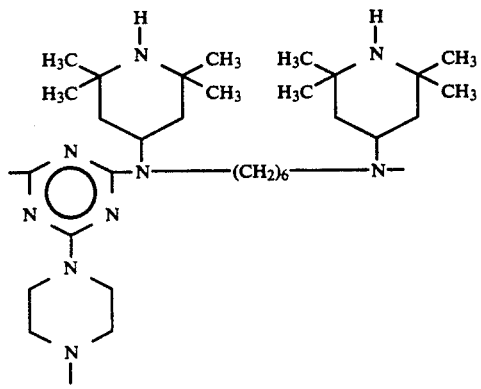

-continued

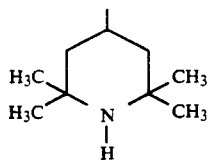

The effectiveness of the compounds according to the present invention as stabilisers is illustrated in the following example in which some compounds obtained in the preparation examples are used for stabilising polypropylene fibres.

EXAMPLE 9

(Light-stabilising action in polypropylene fibres): 2.5 g of each of the products indicated in Table 1, 1.0 g of tris(2,4-di-t-butylphenyl) phosphite, 0.5 g of calcium monoethyl 3,5-di-t-butyl-4-hydroxybenzylphosphonate, 1 g of calcium stearate and 2.5 g of titanium dioxide are mixed in a slow mixer with 1000 g of polypropylene powder of melt index=12 g/10 minutes (measured at 230° C. and 2.16 kg).

The mixtures are extruded at 200°-230° C. to give polymer granules which are then converted into fibres, using a pilot-type apparatus (®Leonard, Sumirago (VA), Italy) and operating under the following conditions:

| | |
|---|---|
| extruded temperature | 200-230° C. |
| head temperature | 255-260° C. |
| stretch ratio | 1:3.5 |
| count | 11 dtex per filament. |

The fibres thus prepared are exposed, mounted on a white card, in a model 65 WR Weather-O-Meter (ASTM D 2565-85) with a black panel temperature of 63° C.

The residual tenacity is measured on samples taken after various times of exposure to light by means of a constant-speed tensometer, and the exposure time in hours ($T_{50}$) needed to halve the initial tenacity is then calculated.

Fibres prepared under the same conditions as indicated above, but without addition of the compounds of the invention, are exposed for comparison.

The results obtained are shown in Table 1:

TABLE 1

| Stabiliser | $T_{50}$ (hours) |
|---|---|
| None | 150 |
| Compound from Example 2 | 1530 |
| Compound from Example 3 | 1750 |
| Compound from Example 6 | 1600 |
| Compound from Example 7 | 1600 |
| Compound from Example 8 | 1650 |

-continued
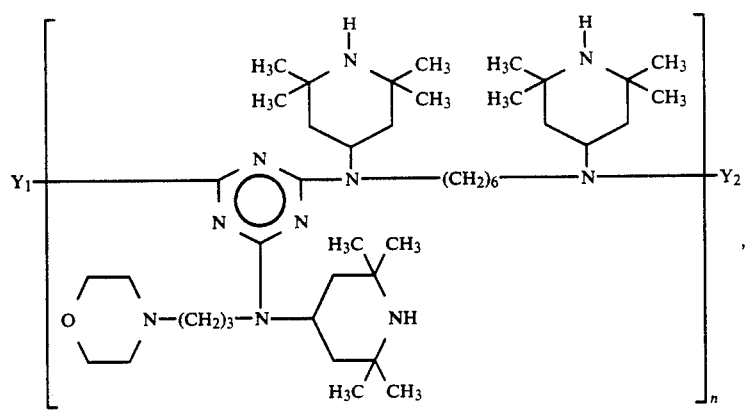
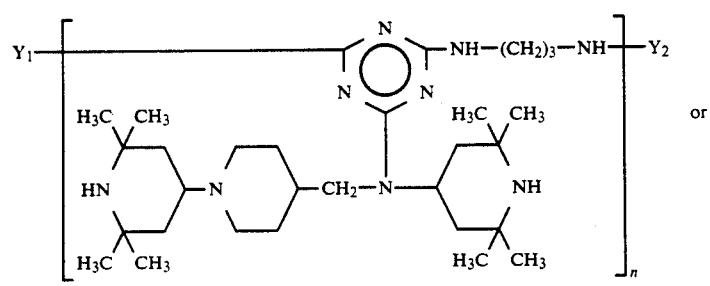
or
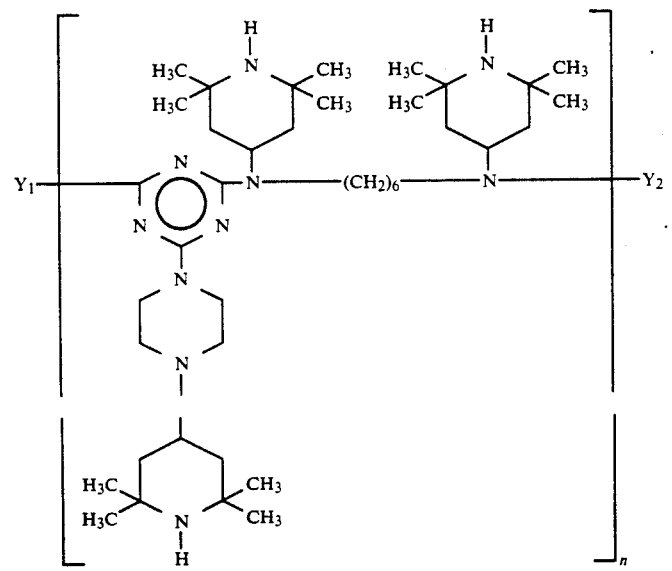

What is claimed is:

1. A compound of formula (I)

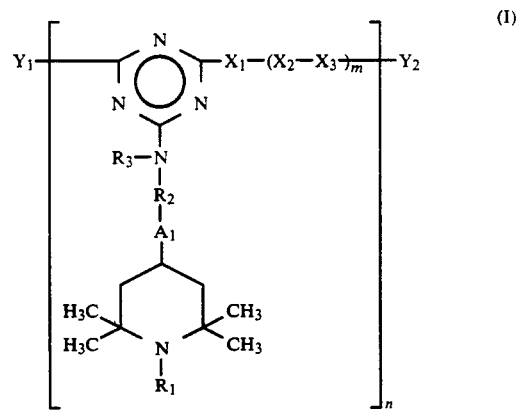

in which $R_1$ is hydrogen, $C_1$-$C_8$alkyl, O·, OH, NO, $CH_2CN$, $C_1$-$C_{18}$alkoxy, $C_5$-$C_{12}$cycloalkoxy, $C_3$-$C_6$alkenyl, $C_7$-$C_9$phenylalkyl which is unsubstituted or mono-, di-or tri-substituted on the phenyl by $C_1$-$C_4$alkyl; or $R_1$ is $C_1$-$C_8$alkanoyl, $C_3$-$C_8$alkenoyl or benzoyl, $A_1$ is —O— or >N—$R_4$ where $R_4$ is methyl, $C_1$-$C_8$alkanoyl, $C_3$-$C_8$alkenoyl, benzoyl or ($C_1$-$C_8$alkoxy)-carbonyl, $R_2$ is $C_2$-$C_{12}$alkylene, $R_3$ is hydrogen, $C_1$-$C_{18}$alkyl, $C_5$-$C_{12}$cycloalkyl which is unsubstituted or mono-, di- or tri-substituted by $C_1$-$C_4$alkyl; $C_7$-$C_9$phenylalkyl which is unsubstituted or mono-, di- or tri-substituted on the phenyl by $C_1$-$C_4$alkyl; or a group of the formula (II)

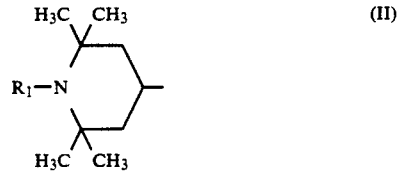

with $R_1$ being as defined above, or —$A_1$—$R_2$— is a direct bond and, in this case, $R_3$ is a group of the formula (III)

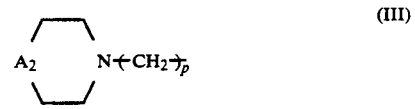

in which $A_2$ is a direct bond, —O—, —$CH_2$—, —$CH_2CH_2$— or >N—$CH_3$ and p is an integer from 2 to 6, or

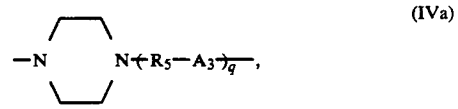

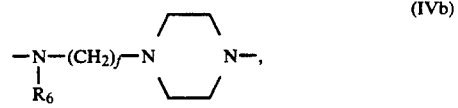

-continued

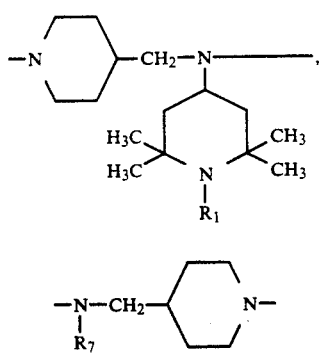  (IVc)

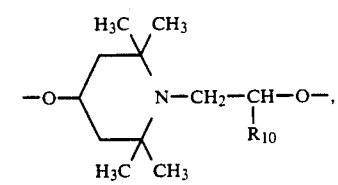  (IVd)

is also one of the groups of the formulae (IVa)—(IVd)

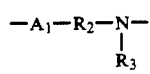

in which $R_5$ is $C_2$-$C_6$alkylene, $A_3$ is —O— or a group $>N$—$R_8$ where $R_8$ is as defined for $R_3$, q is zero or 1, $R_6$ and $R_7$ are as defined for $R_4$, r is an integer from 2 to 6 and $R_1$ is as defined above, $X_1$ and $X_3$ which are identical or different are one of the groups of the formulae (Va)–(Ve)

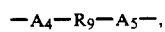  (Va)

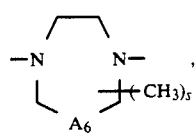  (Vb)

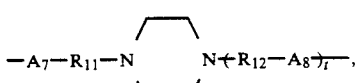  (Vc)

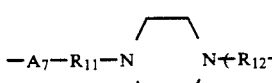  (Vd)

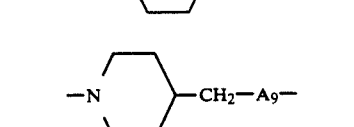  (Ve)

in which $A_4$, $A_5$, $A_7$, $A_8$ and $A_9$ which are identical or different are as defined for $A_3$, $R_9$ is $C_2$-$C_{12}$alkylene, $C_4$-$C_{12}$alkylene interrupted by 1, 2 or 3 oxygen atoms or by 1 or 2 $>N$—$R_{13}$ groups where $R_{13}$ is as defined for $R_3$, or $R_{13}$ is $C_1$-$C_8$alkanoyl, $C_3$-$C_8$alkenoyl, benzoyl or ($C_1$-$C_8$alkoxy)-carbonyl; $C_5$-$C_7$cycloalkylene unsubstituted or mono-substituted by $C_1$-$C_4$alkyl, $C_5$-$C_7$cycloalkylene-di-($C_1$-$C_4$alkylene), $C_1$-$C_4$alkylene-di-($C_5$-$C_7$cycloalkylene), $C_2$-$C_4$alkylidene-di-($C_5$-$C_7$cycloalkylene), phenylene, phenylene-di-($C_1$-$C_4$alkylene), ($C_1$-$C_4$alkylene)-diphenylene or ($C_2$-$C_4$alkylidene)-diphenylene, where each phenylene group is unsubstituted or mono- or di-substituted by $C_1$-$C_4$alkyl, $R_{10}$ is hydrogen, $C_1$-$C_8$alkyl or phenyl, $A_6$ is a direct bond or —CH$_2$—, s is zero, 1, 2 or 3, $R_{11}$ and $R_{12}$ which are identical or different are $C_2$-$C_6$alkylene, and t is zero or 1, $X_2$ is $C_2$-$C_{12}$alkylene, $C_4$-$C_{12}$alkylene interrupted by 1, 2 or 3 oxygen atoms; 2-hydroxytrimethylene, xylylene, carbonyl or one of the groups of the formulae (VIa)–(VIe)

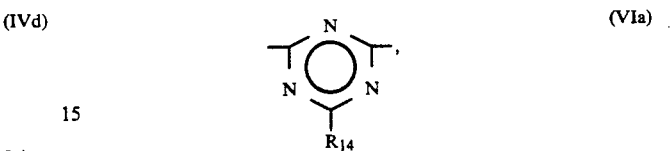  (VIa)

  —CO—$R_{15}$—CO—, (VIb)

  —COO—$R_{16}$—OOC—, (VIc)

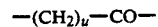  —(CH$_2$)$_u$—CO— (VId)

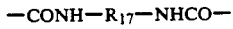  —CONH—$R_{17}$—NHCO— (VIe)

in which $R_{14}$ is a group of the formula (VII)

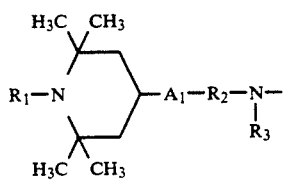  (VII)

in which $R_1$, $A_1$, $R_2$ and $R_3$ are as defined above, or $R_{14}$ is a group —OR$_{18}$, —SR$_{18}$ or

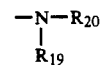

in which $R_{18}$, $R_{19}$ and $R_{20}$ which are identical or different are hydrogen, $C_1$-$C_{18}$alkyl, $C_5$-$C_{12}$cycloalkyl which is unsubstituted or mono-, di- or tri-substituted by $C_1$-$C_4$alkyl; $C_3$-$C_{18}$alkenyl, phenyl which is unsubstituted or mono-, di- or tri-substituted by $C_1$-$C_4$alkyl or $C_1$-$C_4$alkoxy; $C_7$-$C_9$phenylalkyl which is unsubstituted or mono-, di- or tri-substituted on the phenyl by $C_1$-$C_4$alkyl; tetrahydrofurfuryl, a group of the formula (II), $C_2$-$C_4$alkyl substituted in the 2-, 3- or 4-position by $C_1$-$C_8$alkoxy or by di-($C_1$-$C_4$alkyl)-amino or by a group of the formula (III); or the group

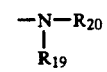

is 1-pyrrolidyl, 1-piperidyl, 4-morpholinyl, 4-methyl-1-piperazinyl or 1-hexahydroazepinyl, $R_{15}$ is a direct bond, $C_1$-$C_{12}$alkylene, cyclohexylene, methylcyclohexylene or phenylene, $R_{16}$ is as defined for $R_9$, u is an integer from 1 to 10 and $R_{17}$ is as defined for $R_9$ or is a group

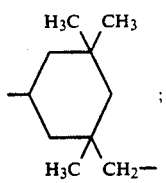

m is zero, 1, 2, 3 or 4,
n is a number from 1 to 50,
$Y_1$ is Cl, OH, ONa, OK, a group $R_{14}$ or $Y_1$ is a group $-X_1Z$ or $-X_3Z$ where Z is hydrogen, methyl, benzyl, $C_1$-$C_8$alkanoyl, $C_3$-$C_8$alkenoyl, benzoyl or ($C_1$-$C_8$alkoxy)-carbonyl and $Y_2$ is Z, a group

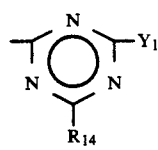

or a group $-X_2OH$, and
when m is 0 and n is 1, the only definition of $Y_1$ is the group $-X_1Z$, with the proviso that the said group $-X_1Z$ is other than the group of the formula

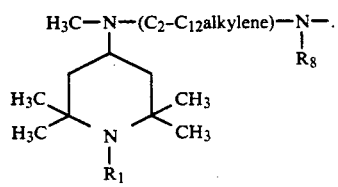

and, in the individual recurrent structural units of the formula (I), each of the groups $R_1$, $A_1$, $R_2$, $R_3$, $X_1$, $X_2$, $X_3$ and m have the same or different definitions.

2. A compound of formula (I) according to claim 1 in which
$A_1$ is $-O-$ or $>N-R_4$, where $R_4$ is methyl, $C_3$-$C_6$alkanoyl, $C_1$-$C_6$alkenoyl, benzoyl or ($C_1$-$C_6$alkoxy)-carbonyl,
$R_2$ is $C_2$-$C_{10}$alkylene,
$R_3$ is hydrogen, $C_1$-$C_{12}$alkyl, $C_5$-$C_8$cycloalkyl which is unsubstituted or mono-, di- or tri-substituted by $C_1$-$C_4$alkyl; benzyl which is unsubstituted or mono-, di- or tri-substituted on the phenyl by $C_1$-$C_4$alkyl; or a group of the formula (II), or $-A_1-R_2-$ is a direct bond and, in this case, $R_3$ is a group of the formula (III) in which $A_2$ is a direct bond, $-O-$ or $-CH_2-$ and p is an integer from 2 to 4, or

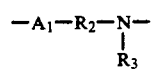

is also one of the groups of the formulae (IVa)-(IVd) in which $R_5$ is $C_2$-$C_4$alkylene, $A_3$ is $-O-$ or an $>N-R_8$ group where $R_8$ is as defined for $R_3$, q is zero or 1, $R_6$ and $R_7$ are as defined for $R_4$, r is an integer from 2 to 4, $X_1$ and $X_3$ which are identical or different are one of the groups of the formulae (Va)-(Ve) in which $A_4$, $A_5$, $A_7$, $A_8$ and $A_9$ which are identical or different are as defined for $A_3$, $R_9$ is $C_2$-$C_{10}$alkylene, $C_4$-$C_{10}$alkylene interrupted by 1,2 or 3 oxygen atoms or by 1 or $2>N-R_{13}$ groups where $R_{13}$ is as defined for $R_3$, or $R_{13}$ is $C_1$-$C_4$alkanoyl, $C_3$-$C_4$alkenoyl or ($C_1$-$C_4$alkoxy)-carbonyl; cyclohexylene, cyclohexylenedimethylene, methylenedicyclohexylene, isopropylidenedicyclohexylene, phenylene, methylphenylene, xylylene, methylenediphenylene or isopropylidenediphenylene, $R_{10}$ is hydrogen, $C_1$-$C_4$alkyl or phenyl, $A_6$ is a direct bond or $-CH_2-$, s is zero, 1, 2 or 3, $R_{11}$ and $R_{12}$ which are identical or different are $C_2$-$C_4$alkylene and t is zero or 1, $X_2$ is $C_2$-$C_{10}$alkylene, $C_4$-$C_{10}$alkylene interrupted by 1, 2 or 3 oxygen atoms; 2-hydroxytrimethylene, xylylene or one of the groups of the formulae (VIa)-(VIe) in which $R_{14}$ is a group of the formula (VII) or a group $-OR_{18}$, $-SR_{18}$ or

in which $R_{18}$, $R_{19}$ and $R_{20}$ which are identical or different are hydrogen, $C_1$-$C_{12}$alkyl, $C_5$-$C_8$cycloalkyl which is unsubstituted or mono-, di-or tri-substituted by $C_1$-$C_4$alkyl; $C_3$-$C_{12}$alkenyl, phenyl which is unsubstituted or mono-, di- or trisubstituted by $C_1$-$C_4$alkyl or $C_1$-$C_4$alkoxy; benzyl which is unsubstituted or mono-, di- or tri-substituted on the phenyl by $C_1$-$C_4$alkyl; tetrahydrofurfuryl, a group of the formula (II), $C_2$-$C_3$alkyl substituted in the 2- or 3-position by $C_1$-$C_4$alkoxy or by di-($C_1$-$C_4$alkyl)-amino or by a group of the formula (III); or the group

is 1-pyrrolidyl, 1-piperidyl, 4-morpholinyl, 4-methyl-1-piperazinyl or 1-hexahydroazepinyl, $R_{15}$ is a direct bond, $C_1$-$C_{10}$alkylene, cyclohexylene or phenylene, $R_{16}$ is as defined for $R_9$, u is an integer from 1 to 5, $R_{17}$ is as defined for $R_9$ or is a group

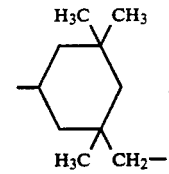

m is zero, 1, 2 or 3, n is a number from 1 to 30, $Y_1$ is Cl, OH, ONa, OK, a group $R_{14}$ or a group $-X_1Z$ or $-X_3Z$ where Z is hydrogen, methyl, benzyl, $C_1$-$C_4$alkanoyl, $C_3$-$C_4$alkenoyl or ($C_1$-$C_4$alkoxy)-carbonyl and $Y_2$ is Z, a group

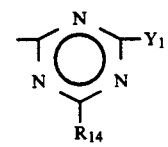

or a group $-X_2OH$.

3. A compound of the formula (I) according to claim 1, in which $R_1$ is hydrogen, $C_1$-$C_4$alkyl, OH, $C_6$-$C_{12}$alkoxy, $C_5$-$C_8$cycloalkoxy, allyl, benzyl or acetyl.

4. A compound of the formula (I) according to claim 1, in which $A_1$ is —O— or >N—$R_4$, where $R_4$ is methyl, $C_1$-$C_4$alkanoyl, $C_3$-$C_4$alkenoyl, benzoyl or ($C_1$-$C_4$alkoxy)-carbonyl, $R_2$ is $C_2$-$C_8$alkylene, $R_3$ is hydrogen, $C_1$-$C_8$alkyl, cyclohexyl which is unsubstituted or mono-, di- or tri-substituted by $C_1$-$C_4$alkyl; benzyl or a group of the formula (II), or —$A_1$—$R_2$— is a direct bond and, in this case, $R_3$ is a group of the formula (III) in which $A_2$ is —O— or —$CH_2$— and p is 2 or 3, or

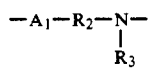

is also one of the groups of the formulae (IVa)-(IVd) in which $R_5$ is $C_2$-$C_3$alkylene, $A_3$ is —O— or an >N—$R_8$ group where $R_8$ is as defined for $R_3$, q is zero or 1, $R_6$ and $R_7$ are as defined for $R_4$, r is 2 or 3, $X_1$ and $X_3$ which are identical or different are one of the groups of the formulae (Va)-(Ve) in which $A_4$, $A_5$, $A_7$, $A_8$ and $A_9$ which are identical or different are as defined for $A_3$, $R_9$ is $C_2$-$C_8$alkylene, $C_4$-$C_{10}$alkylene interrupted by 1, 2 or 3 oxygen atoms or by an >N—$R_{13}$ group with $R_{13}$ being hydrogen, methyl, acetyl or ($C_1$-$C_2$alkoxy)-carbonyl; cyclohexylene, cyclohexylenedimethylene, methylenedicyclohexylene, xylylene or isopropylidenediphenylene, $R_{10}$ is hydrogen, methyl or phenyl, $A_6$ is a direct bond or —$CH_2$—, s is zero, 1, 2 or 3, $R_{11}$ and $R_{12}$ which are identical or different are $C_2$-$C_3$alkylene and t is zero or 1, $X_2$ is $C_2$-$C_8$alkylene, $C_4$-$C_8$alkylene interrupted by 1 or 2 oxygen atoms; 2-hydroxytrimethylene, xylylene or one of the groups of the formulae (VIa)-(VIe) in which $R_{14}$ is a group of the formula (VII) or a group —$OR_{18}$, —$SR_{18}$ or

where $R_{18}$, $R_{19}$ and $R_{20}$ which are identical or different are hydrogen, $C_1$-$C_8$alkyl, cyclohexyl which is unsubstituted or mono-, di- or tri-substituted by $C_1$-$C_4$alkyl; allyl, undecenyl, phenyl, benzyl, tetrahydrofurfuryl, a group of the formula (II), $C_2$-$C_3$-alkyl substituted in the 2- or 3-position by $C_1$-$C_4$alkoxy, by dimethylamino or by diethylamino or by a group of the formula (III); or the group

is 4-morpholinyl, $R_{15}$ is a direct bond, $C_1$-$C_8$alkylene, cyclohexylene or phenylene, $R_{16}$ is $C_2$-$C_8$alkylene, $C_4$-$C_{10}$alkylene interrupted by 1, 2 or 3 oxygen atoms; cyclohexylenedimethylene, isopropylidenedicyclohexylene or isopropylidenediphenylene, u is an integer from 1 to 4, $R_{17}$ is as defined for $R_9$ or is methylphenylene, methylenediphenylene or a group

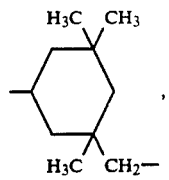

m is zero, 1, 2 or 3, n is a number from 1 to 20, $Y_1$ is OH, ONa, OK, a group $R_{14}$ or a group —$X_1Z$ or —$X_3Z$ where Z is hydrogen, methyl, acetyl or ($C_1$-$C_2$alkoxy)-carbonyl and $Y_2$ is Z, a group

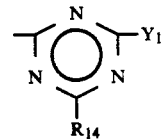

or a group —$X_2OH$.

5. A compound of the formula (I) according to claim 1, in which $A_1$ is —O—or >N-$R_4$, where $R_4$ is methyl, acetyl or ($C_1$-$C_2$alkoxy)-carbonyl, $R_2$ is $C_2$-$C_6$alkylene, $R_3$ is hydrogen, $C_1$-$C_4$alkyl, cyclohexyl, benzyl or a group of the formula (II), or —$A_1$—$R_2$—is a direct bond and, in this case, $R_3$ is a group of the formula (III) in which $A_2$ is —O—and p is 2 or 3, or

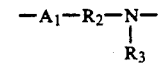

is also one of the groups of the formulae (IVa)-(IVd) in which $R_5$ is $C_2$-$C_3$alkylene, $A_3$ is —O—or an >N—$R_8$ group where $R_8$ is as defined for $R_3$, q is zero or 1, $R_6$ and $R_7$ are as defined for $R_4$, r is 2 or 3, $X_1$ and $X_3$ which are identical or different are one of the groups of the formulae (Va)-(Ve) in which $A_4$, $A_5$, $A_7$, $A_8$ and $A_9$ which are identical or different are as defined for $A_3$, $R_9$ is $C_2$-$C_6$alkylene, $C_6$-$C_{10}$alkylene interrupted by 2 or 3 oxygen atoms; cyclohexylenedimethylene, methylenedicyclohexylene or xylylene, $R_{10}$ is hydrogen or methyl, $A_6$ is a direct bond, s is zero or 1, $R_{11}$ and $R_{12}$ are ethylene or trimethylene and t is zero or 1, $X_2$ is $C_2$-$C_6$alkylene, 2-hydroxytrimethylene, xylylene or one of the groups of the formulae (VIa)-(VIe) in which $R_{14}$ is a group of the formula (VII) or a group —$OR_{18}$ or

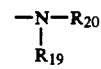

in which $R_{18}$ is $C_1$-$C_4$alkyl, cyclohexyl, allyl, phenyl, benzyl, tetrahydrofurfuryl or a group of the formula (II), $R_{19}$ and $R_{20}$ which are identical or different are as defined above for $R_{18}$ or are hydrogen or $C_2$-$C_3$alkyl substituted in the 2- or 3-position by methoxy, by ethoxy, by dimethylamino or by diethylamino or by a group of the formula (III); or the group

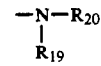

is 4-morpholinyl, $R_{15}$ is a direct bond or $C_1$-$C_8$alkylene, $R_{16}$ is $C_4$-$C_6$alkylene, u is 1 or 2, $R_{17}$ is $C_2$-$C_6$alkylene or a group

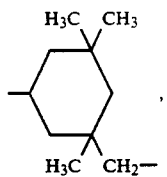

m is zero, 1 or 2, n is a number from 1 to 15, $Y_1$ is OH, ONa, OK, a group $R_{14}$ or a group —$X_1Z$ or —$X_3Z$ where Z is hydrogen, methyl, acetyl or ($C_1$-$C_2$alkoxy)-carbonyl and $Y_2$ is Z, a group

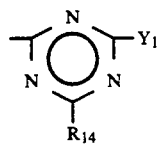

or a group —$X_2$OH.

6. A compound of the formula (I) according to claim 1, in which $R_1$ is hydrogen or methyl, $A_1$ is —O— or >N—CH$_3$, $R_2$ is —(CH$_2$)$_{2-6}$—, $R_3$ is hydrogen, methyl, 2,2,6,6-tetramethyl-4-piperidyl or 1,2,2,6,6-pentamethyl-4-piperidyl, or —$A_1$—$R_2$— is a direct bond and, in this case, $R_3$ is a group

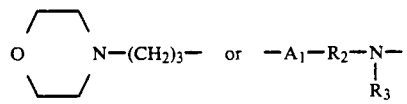

is also one of the groups of the formulae (IVa)-(IVc) in which $R_5$ is ethylene, $A_3$ is —O— or >N—$R_8$, where $R_8$ is a defined for $R_3$, q is zero or 1, $R_6$ is methyl, r is 2, $X_1$ and $X_3$ which are identical or different are a group of the formula (Va) or (Vb) in which $A_4$ and $A_5$ which are identical or different are an >N—$R_8$ group where $R_8$ is as defined for $R_3$, $R_9$ is —(CH$_2$)$_{2-6}$— or —(CH$_2$)$_3$—O—(CH$_2$)$_{2-4}$—O—(CH$_2$)$_3$— and $R_{10}$ is hydrogen or methyl, $X_2$ is 2-hydroxytrimethylene or a group of the formula (VIa) where $R_{14}$ is a group of the formula (VII), m is zero or 1, n is a number from 1 to 10, $Y_1$ is OH, ONa, OK, a group $R_{14}$ or a group —$X_1Z$ or —$X_3Z$ with Z being hydrogen or methyl and $Y_2$ is hydrogen, methyl or a group

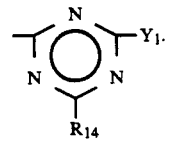

7. A compound of the formula (I) according to claim 1, in which $R_1$ is hydrogen or methyl, $A_1$ is >N—CH$_3$, $R_2$ is —(CH$_2$)$_{2-6}$—, $R_3$ is 2,2,6,6-tetramethyl-4-piperidyl or 1,2,2,6,6-pentamethyl-4-piperidyl, or —$A_1$—$R_2$— is a direct bond and, in this case, $R_3$ is a group

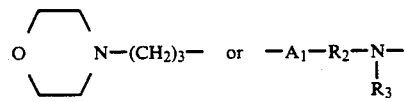

is a group of the formula (IVa) or (IVc), q and m are zero, $X_1$ is a group of the formula (Va) in which $A_4$ and $A_5$ which are identical or different are an >N—$R_8$ group where $R_8$ is hydrogen, 2,2,6,6-tetramethyl-4-piperidyl or 1,2,2,6,6-pentamethyl-4-piperidyl, $R_9$ is —(CH$_2$)$_{2-6}$— and n is a number from 1 to 10.

8. A compound of the formula (I) according to claim 1, which corresponds to

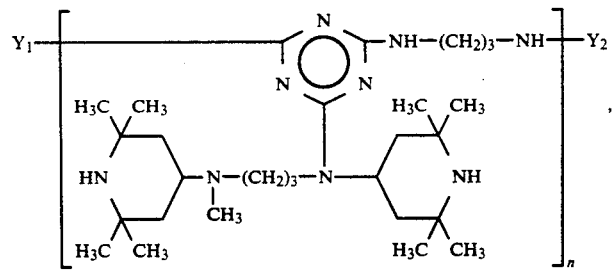

,

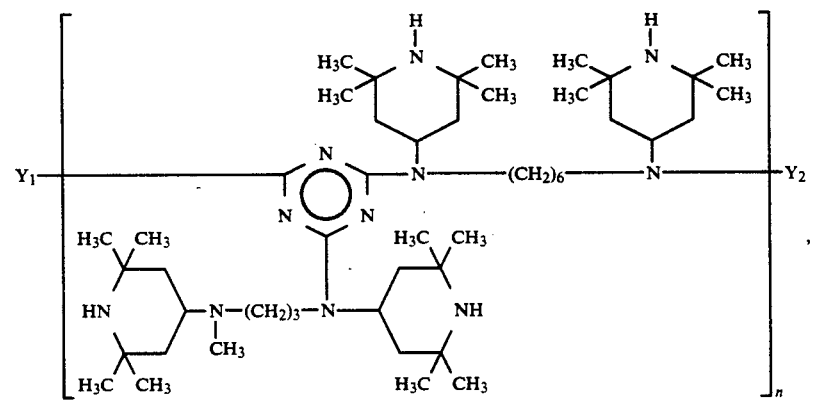

,